United States Patent [19]

McIntosh

[11] 4,033,749
[45] July 5, 1977

[54] ALKOXYCARBONYLPHOSPHONIC ACID DERIVATIVE BRUSH CONTROL AGENTS

[75] Inventor: Colin Leslie McIntosh, Newark, Del.

[73] Assignee: E. I, Du Pont de Nemours and Company, Wilmington, Del.

[22] Filed: Sept. 25, 1975

[21] Appl. No.: 616,837

Related U.S. Application Data

[63] Continuation-in-part of Ser. No. 474,536, May 30, 1974, Pat. No. 3,943,201, which is a continuation-in-part of Ser. No. 397,723, Sept. 17, 1973, abandoned, which is a continuation-in-part of Ser. No. 381,620, July 23, 1973, abandoned.

[52] U.S. Cl. .................................. 71/86; 71/76; 71/87
[51] Int. Cl.² ............................................ A01N 9/36
[58] Field of Search .................... 71/86, 87, 76

[56] References Cited

UNITED STATES PATENTS

| 3,005,010 | 10/1961 | Grisley, Jr. | 71/86 X |
| 3,033,891 | 5/1962 | Grisley, Jr. | 71/87 X |
| 3,619,166 | 11/1971 | Quebedeaux, Jr. | 71/86 |
| 3,627,507 | 12/1971 | Langsdorf, Jr. | 71/86 X |

*Primary Examiner*—Joseph Paul Brust

[57] ABSTRACT

Alkoxycarbonylphosphonic acids and alkylthiocarbonylphosphonic acids and esters and salts of these acids such as diammonium methoxycarbonylphosphonate are useful for regulation of the growth rate of plants.

9 Claims, No Drawings

ALKOXYCARBONYLPHOSPHONIC ACID DERIVATIVE BRUSH CONTROL AGENTS

CROSS-REFERENCE TO RELATED APPLICATION

This application is a continuation-in-part of my copending application Ser. No. 474,536, filed May 30, 1974, now U.S. Pat. No. 3,943,201, which in turn is a continuation-in-part of my copending application Ser. No. 397,723, filed Sept. 17, 1973, now abandoned, which in turn is a continuaton-in-part of my copending application Ser. No. 381,620, filed July 23, 1973, now abandoned.

BACKGROUND OF THE INVENTION

This invention relates to novel alkoxycarbonylphosphonic acids and (alkylthio)carbonylphosphonic acids and their use as plant growth regulants. The use of various carbamoylphosphonates for control of plant growth is known. For example, see U.S. Pat. No. 3,627,507 and German Offenlegungsschrift 2,040,367. However, neither of these references suggests the compounds of this invention. Further, some of the active compounds within the scope of this invention are known. U.S. Pat. No. 3,033,891 discloses esters and salts of (alkylthio)carbonylphosphonic acid, but the reference does not suggest the plant growth regulant activity of these compounds.

SUMMARY OF THE INVENTION

Compounds of the formula

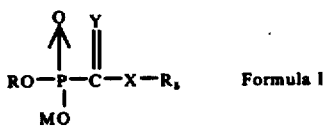

Formula I wherein
R is M; alkyl of 1 to 8 carbon atoms, optionally substituted with a chlorine, bromine, fluorine or iodine; alkenyl of 3 to 8 carbon atoms; or

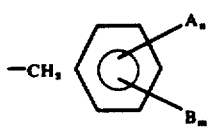

wherein
A is chlorine or methyl,
B is chlorine or methyl,
n is 0 or 1, and
m is 0 or 1;
$R_5$ is alkyl of 1 to 6 carbon atoms, alkenyl of 3 to 4 carbon atoms, or benzyl;
X is oxygen or sulfur;
Y is oxygen or sulfur, provided that when Y is sulfur, X is sulfur; and when X is sulfur, R is not hydrogen;
M is hydrogen, sodium, lithium, potassium, calcium, magnesium, zinc, manganese, barium, or

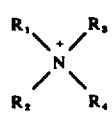

wherein $R_1$ is hydrogen, alkyl of 1 to 4 carbon atoms, or hydroxyalkyl of 2 to 4 carbon atoms;
$R_2$ is hydrogen, alkyl of 1 to 4 carbon atoms, or hydroxyalkyl of 2 to 4 carbon atoms;
$R_3$ is hydrogen, alkyl of 1 to 4 carbon atoms, or hydroxyalkyl of 2 to 4 carbon atoms; and
$R_4$ is hydrogen or alkyl of 1 to 12 carbon atoms, provided that the total number of carbon atoms in $R_1$, $R_2$, $R_3$, and $R_4$ is less than 16
are useful as plant growth regulants. These compounds and salts are particularly useful for retarding the growth of woody plants. The compounds and salts can be applied to plants by directly contacting the plants with the compounds or by applying the compounds or salts to the soil in which the plants grow. Both of these modes of application are encompassed within the term "applying to plants" as used herein.

Preferred compounds of this invention include those compounds of Formula I where
R is alkyl of 1 to 4 carbons, benzyl or M;
M is hydrogen, sodium, potassium or ammonium;
$R_5$ is alkyl of 1 to 3 carbons;
X is oxygen or sulfur, provided that when X is sulfur, R is not hydrogen; and
Y is oxygen.

The most preferred compounds of this invention are methoxycarbonylphosphonic acid, diammonium methoxycarbonylphosphonate, ethyl sodium methoxycarbonylphosphonate, and methyl sodium methoxycarbonylphosphonate.

The compounds of this invention having the formula

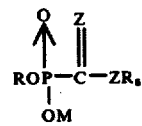

where Z is oxygen or sulfur and R, M and $R_5$ are defined as above, provided that when Z is sulfur, R is not hydrogen, are novel.

DESCRIPTION OF THE PREFERRED EMBODIMENTS

The alkoxycarbonylphosphonic acids and (alkylthio)carbonylphosphonic acids of this invention are readily prepared by the interaction of dialkyl alkoxycarbonylphosphonates or (alkylthio)carbonylphosphonates with hydrogen iodide. Salts of these acids are prepared by reacting the acids with one or two equivalents of a base having the appropriate cation.

The dialkyl alkoxycarbonylphosphonates and (alkylthio)carbonylphosphonates which are precursors to the compounds of this invention can be prepared by a variety of methods available in the literature, such as Nylen, Chem, Ber. 57, 1023 (1924), and Reetz et al., JACS 77, 3813 (1955). The method comprises treating an appropriate trialkyl phosphite with a chloroformate or thiolchloroformate.

The following Examples further illustrate the preparation of the compounds of this invention.

EXAMPLE 1

Into a stirred solution comprised of 14.8 parts of dimethyl methoxycarbonylphosphonate and 100 parts of methylene chloride at $(-)5° - (+)5°$ C was added 30 parts of anhydrous hydrogen iodide. The reaction was then allowed to warm to room temperature whereupon it was stirred overnight. The bottom layer which formed was separated and evaporated under reduced pressure to afford 6.7 parts of methoxycarbonylphosphonic acid. The nmr spectrum (dmso-d$_6$) exhibited none of the P-O-CH$_3$ doublet, but retained the COOCH$_3$ signal. The ir showed the

at 1700 cm$^{-1}$ and the P—O at 1100 cm$^{-1}$.

By replacing the dimethyl methoxycarbonylphosphonate of Example 1 with the appropriate dimethyl alkoxycarbonyl- or (alkylthio)carbonylphosphonate, the following compounds can be prepared.

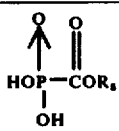

| R$_1$ |
|---|
| CH$_2$=CHCH$_2$CH$_2$ |
| CH$_2$=CHCH$_2$ |
| CH$_3$CH$_2$ |
| (CH$_3$)$_2$CHCH$_2$ |
| CH$_3$CH$_2$CH$_2$CH$_2$CH$_2$CH$_2$ |
| C$_6$H$_5$CH$_2$ |
| CH$_3$CH$_2$CH$_2$CH$_2$CH$_3$ |

EXAMPLE 2

To 50 parts of ammonium hydroxide containing a few pieces of ice was added with stirring 3 parts of methoxycarbonylphosphonic acid, the product of Example 1. The cooled solution was allowed to stir for 15 minutes and was then evaporated under reduced pressure to afford the desired diammonium methoxycarbonylphosphonate, m.p. 157° d.

By replacing the ammonium hydroxide of Example 2 with one or two equivalents of the appropriate base or by routine cation exchange procedures, the following salts could similarly be prepared:

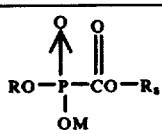

| R$_1$ | R | M |
|---|---|---|
| CH$_3$ | Na | H |
| CH$_3$ | Na | Na |
| CH$_3$ | NH$_4$ | H |
| CH$_3$CH$_2$ | Ca | Ca |
| CH$_3$CH$_2$CH$_2$CH$_2$CH$_2$CH$_3$ | Li | Li |
| CH$_3$ | ½ Mn | ½ Mn |
| CH$_3$CH$_2$CH$_3$ | ½ Zn | ½ Zn |
| C$_6$H$_5$CH$_2$ | ½ Ba | ½ Ba |
| CH$_3$ | ½ Mg | ½ Mg |
| CH$_3$ | (CH$_3$CH$_2$OH)$_3$NH | H |
| CH$_3$ | (CH$_3$)$_3$NH$_3$ | (CH$_3$)$_3$NH$_3$ |
| CH$_3$ | (C$_{12}$H$_{25}$)NH$_3$ | H |
| CH$_3$ | (CH$_3$)$_3$N(C$_{12}$H$_{25}$) | H |
| CH$_2$=CHCH$_2$— | Na | Na |

EXAMPLE 3

A mixture of 15.0 parts of sodium iodide and 8.4 parts of dimethyl methoxycarbonylphosphanate on 20 parts of 2-butanone was heated to 60° for 1 hour. The mixture was cooled and filtered to provide 8.0 parts of the desired methyl sodium methoxycarbonylphosphonate, mp 183° d.

EXAMPLE 4

Ethyl Sodium Methoxycarbonylphosphonate

A solution of 5.9 parts of diethyl methoxycarbonylphosphonate and 4.5 parts of sodium iodide was stirred at room temperature in 50 parts of tetrahydrofuran for 60 hours. The resulting mixture was filtered to give 3.5 parts of the desired ethyl sodium methoxycarbonylphosphonate, m.p. 123° d.

In a similar manner, the following salts can be prepared from the dialkyl alkoxycarbonylphosphonates.

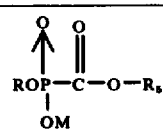

| R | R$_1$ | M | M.P., ° C. |
|---|---|---|---|
| C$_6$H$_5$CH$_2$ | CH$_3$— | Na | 198–204 |
| CH$_2$=CHCH$_2$ | CH$_3$— | Na | >300 |
| CH$_3$CH$_2$CH$_2$CH$_2$ | CH$_2$CH$_3$ | Na | 248 d |
| CH$_3$CH$_2$CH$_2$CH$_2$ | CH$_3$CH$_2$CH$_2$CH$_2$CH$_2$CH$_3$ | Na | Wax |
| CH$_3$ | CH$_3$CH$_2$CH$_2$CH$_2$CH$_2$CH$_3$ | Na | 73–8 |
| CH$_3$ | (CH$_3$)$_2$CHCH$_2$ | Na | 154–6 |
| CH$_3$CH$_2$ | C$_6$H$_5$CH$_2$ | Na | >300 |
| ClCH$_2$CH$_2$ | CH$_3$— | Na | — |
|  | CH$_3$CH$_2$ | Na | — |
| (2,6-dichloro-methylphenyl group) |  |  |  |
| CH$_3$CH$_2$CH$_2$CH$_2$CHCH$_3$ (with CH$_3$ branch) | CH$_3$— | Na | — |
| CH$_3$CH$_2$CH$_2$CH$_2$CH$_2$CH$_3$ | CH$_2$CH$_3$ | Na | — |
| FCH$_2$CH$_2$— | CH$_3$— | Na | — |
| ICH$_2$CH$_2$— | CH$_3$— | Na | — |
| BrCH$_2$CH$_2$— | CH$_3$— | Na | — |

EXAMPLE 5

Passage of an aqueous solution of ethyl sodium methoxycarbonylphosphonate through an appropriate acid ion exchange column gives ethyl hydrogen methoxycarbonylphosphonate.

In a similar manner, the following hydrogen phosphonates can be prepared from the appropriate salts.

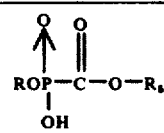

| R | R$_1$ |
|---|---|
| CH$_3$— | CH$_3$— |
|  | CH$_3$CH$_2$ |
| (chloro-methylphenyl group) |  |
| CH$_3$— | CH$_3$CH$_2$ |
| CH$_3$CH$_2$CH$_2$CH$_3$ | CH$_3$CH$_2$ |

-continued

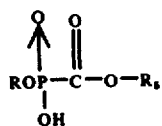

| R | R₁ |
|---|---|
| CH₃CH₂CH₂CH₂CHCH₃<br>    \|<br>    CH₂<br>    \|<br>    CH₃ | CH₃— |
| CH₃—<br>CH₂=CHCH₂<br>ClCH₂CH₂<br>CH₃CH₂ | C₆H₅CH₂<br>CH₃CH₂<br>CH₃CH₂<br>CH₂=CHCH₂CH₂ |
| CH₂=CCH₃<br>    \|<br>    CH₃ | CH₃— |
| CH₃CH₂CH₂CH₂CH₂CH₃<br>CH₃CH₂<br>CH₃—<br>CH₃— | CH₃—<br>C₆H₅CH₂<br>CH₃CH₂CH₂CH₂CH₂CH₃—<br>—CH₂—CH=CH₂ |

EXAMPLE 6

Careful neutralization of an aqueous solution of methyl hydrogen methoxycarbonylphosphonate with one equivalent of ammonium hydroxide gives the methyl ammonium methoxycarbonylphosphonate.

In a similar manner, the following phosphonate salts can be prepared from the appropriate hydrogen phosphonate and the appropriate base.

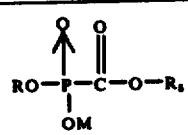

| R | R₁ | M |
|---|---|---|
| CH₃CH₂ | CH₃— | K |
| CH₃CH₂CH₂CH₂CHCH₃<br>    \|<br>    CH₂<br>    \|<br>    CH₃ | CH₃— | Na |
| (CH₃)₂CHCH₂ | CH₃— | Li |
| CH₃— | CH₃CH₂CH₂CH₃ | ¼ Ba |
| ClCH₂CH₂ | CH₃CH₂CH₃ | NH₄ |
| CH₃CH₂CH₂CH₂CH₂CH₃ | CH₂=CHCH₂ | (HOCH₂CH₂)₃NH |
| CH₃— | C₆H₅CH₂ | (C₁₂H₂₅)NH₂ |
| C₆H₅CH₂ | CH₃— | K |
| CH₂=CH—CH₂ | CH₃— | Na |

Alternately, these salts can be prepared directly from the sodium salts by conventional ion exchange methods.

EXAMPLE 7

Using the procedure described in U.S. Pat. No. 3,033,891, the following sodium salts can be prepared.

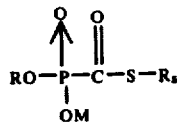

| R | R₁ | M | M.P., °C. |
|---|---|---|---|
| CH₂=CHCH₂ | CH₃— | Na | 157° d |
| CH₃CH₂CH₂CH₃ | CH₃— | Na | Wax |
| C₆H₅CH₂ | CH₃CH₂ | Na | — |
| CH₃CH₂CH₂CH₂CH₂CH₃ | CH₃— | Na | — |
| CH₃— | CH₃C₆H₅ | Na | — |
| CH₃CH₃ | CH₂=CHCH₂ | Na | — |
| (CH₃)₂CHCH₂ | CH₃CH₂CH₂CH₂CH₂CH₃ | Na | — |

EXAMPLE 8

Ethyl Hydrogen (Methylthio)carbonylphosphonate

Passage of an aqueous solution of ethyl sodium (methylthio)carbonylphosphonate prepared as described in U.S. Pat. No. 3,033,891 through an appropriate acid ion exchange resin gives ethyl hydrogen (methylthio)-carbonylphosphonate.

In a similar manner, the following hydrogen phosphonates can be prepared from the appropriate salts.

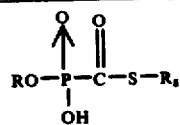

| R | R₁ |
|---|---|
| CH₃— | CH₃CH₂CH₂CH₃ |
| CH₃CH₂CH₂CH₃ | CH₃CH₃ |
| CH₂=CHCH₂ | CH₃CH₂CH₂CH₂CH₂CH₃ |
| CH₃CH=CHCH₂ | CH₃— |
| CH₃=CH—CH₂CH₃ | CH₃CH₂ |
| CH₃CH₂ | CH₂=CHCH₂ |
| C₆H₅CH₂ | CH₃— |
| ClCH₂CH₂ | CH₃CH₂ |

EXAMPLE 9

Methyl potassium (benzylthio)carbonylphosphonate

Careful neutralization of an aqueous solution of methyl hydrogen (benzylthio)carbonylphosphonate with one equivalent of potassium hydroxide gives methyl potassium (benzylthio)carbonylphosphonate.

In a similar manner, the following salts can be prepared from the appropriate hydrogen phosphonate and the appropriate base.

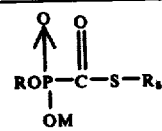

| R | R₁ | M |
|---|---|---|
| CH₃— | CH₃— | K |
| CH₃CH₂ | CH₂=CHCH₂ | NH₄ |
| (CH₃)₂CHCH₂ | CH₃— | (HOCH₂CH₂)₃NH |
| C₆H₅CH₂ | CH₃CH₂ | ¼ Mn |
| ClCH₂CH₂ | CH₃— | Li |
| CH₃CH₂CH₂CH₂CH₂CH₂ | CH₃CH₂ | ¼ Ba |
| CH₂=CHCH₂ | CH₃— | (CH₃)₂NH |

Alternately, these compounds can be prepared by conventional ion exchange methods directly from the sodium salts.

EXAMPLE 10

Ethyl sodium (methylthio)thiocarbonylphosphonate

To a solution of 2.3 parts of diethyl (methylthio)thiocarboylphosphonate in 50 parts of dry tetrahydrofuran was added 1.5 parts of sodium iodide. The solution was stirred for 18 hours at room temperature, then warmed on a steam bath for one-half hour. The desired orange ethyl sodium (methylthio)thiocarbonylphosphonate was then filtered, m.p. 288° d.

EXAMPLE 11

Ethyl hydrogen (methylthio)thiocarbonylphosphonate

Passage of an aqueous solution of ethyl sodium (methylthio)thiocarbonylphosphonate through an appropriate acid ion exchange column gives ethyl hydrogen (methylthio)thiocarboylphosphonate.

In a similar manner by use of the appropriate phosphonate salt, the following compounds can be prepared.

$$RO-\overset{O}{\underset{OH}{P}}-\overset{S}{C}S-R_1$$

| R | $R_1$ |
|---|---|
| $CH_3-$ | $CH_3-$ |
| $CH_3-$ | $CH_3CH_2CH_2CH_3$ |
| $CH_3CH_2$ | $CH_2=CHCH_2$ |
| $CH_3CH_2$ | $C_6H_5CH_2$ |
| $CH_3-$ | $CH_2=CCH_3$ |
|  | $\mid$ |
|  | $CH_3$ |
| $CH_3CH_2CH_2CH_2$ | $CH_3-$ |
| $CH_2=CHCH_2$ | $CH_3CH_2$ |
| $C_6H_5CH_2$ | $CH_3-$ |
| $ClCH_2CH_2$ | $CH_3CH_2CH_2$ |
| $CH_3CH_2CH_2CH_2CHCH_3$ | $CH_3-$ |
| $\mid$ |  |
| $CH_2$ |  |
| $\mid$ |  |
| $CH_3$ |  |

EXAMPLE 12

Methyl barium (methylthio)thiocarbonylphosphonate

Careful neutralization of methyl hydrogen (methylthio)thiocarbonylphosphonate with one-half equivalent of barium carbonate gives methyl barium (methylthio)thiocarbonylphosphonate.

In a similar manner, the following phosphonate salts can be prepared from the appropriate hydrogen phosphonate and the appropriate base.

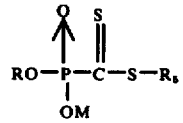

| R | $R_1$ | M |
|---|---|---|
| $(CH_3)_2CHCH_2$ | $CH_3-$ | $NH_4$ |
| $CH_3-$ | $CH_3CH_2$ | K |
| $CH_2=CHCH_2$ | $CH_3-$ | $(C_{18}H_{36})NH_3$ |
| $CH_3-$ | $CH_3CH_2CH_2CH_3$ | ½ Zn |
| $CH_3-$ | $(CH_3)_2CHCH_2$ | $(HOCH_2CH_2)_3NH$ |
| $CH_3CH_2$ | $C_6H_5CH_2$ | ½ Mg |
| $C_6H_5CH_2$ | $CH_3-$ | Li |
| $CH_3CH_2CH_2CH_2CH_2CH_2$ | $CH_3CH_2$ | K |

Alternately, these salts can be prepared directly from the sodium salts by conventional ion exchange methods.

The compounds and salts of the invention are useful for modifying the growth of plants. The compounds and salts of this invention are particularly useful for preventing bud break and retarding the growth of woody plants. Thus, the compounds and salts of this invention can be applied in areas such as power line rights-of-way where low-growing and slow-growing vegetation is especially desirable.

In addition to their value as plant growth retardants, the compounds and salts of this invention can also be used to control flowering, fruit set, and coloration on apples and other fruits. They are useful in controlling the growth of viney plants such as morning glory and Black Valentine bean, and grasses such as crabgrass, barnyard grass, and corn.

The compounds and salts of this invention can also be used to prolong the dormancy of perennial plants and thereby protect the unsprouted buds from frost damage. This can be especially important in the protection of flower buds, which in some years may sprout early and be killed by cold temperatures. Application to plants in the stage where next year's buds are being initiated or are developing gives marked retardation of bud break the following spring and greatly reduced growth.

To illustrate the growth retardant activity of the compounds and salts of this case, the following data are presented.

In one test, the test compounds were applied in a solvent with a wetting agent and a humectant to cotton plants (five-leaf stage including cotyledons), bush bean (second trifoliate leaf expanding), morning glory (four-leaf stage including cotyledons), cockebur (Xanthium sp., four-leaf stage including cotyledons), Cassia tora (three leaves including cotyledons), nutsedge (Cyperus rotundus, three- to five-leaf stage), crabgrass (Digitaria sp., two-leaf stage), barnyard grass (Echinochloa sp., two-leaf stage), wild oats (Avena fatua, one-leaf stage), wheat (two-leaf stage), corn (three-leaf stage), soybean (two-cotyledons), rice (two-leaf stage), and sorghum (three-leaf stage).

Treated plants and controls were maintained in a greenhouse for 16 days; then all species were compared with controls and visually rated for response to treatment.

POST EMERGENCE

| Bush | Morning | Cock- | Nut- | Crab- |

-continued

| COMPOUND | POST EMERGENCE Kg/Ha | Bean | Cotton | Glory | lebur | Cassia | sedge | grass |
|---|---|---|---|---|---|---|---|---|
| H₃COPCOCH₃ (OO/‖‖) OH  Na⁺ | 2 | 8G 2H 6F | 8G | 9C | 7G 2C | 6G | 0 | 0 |
| HOPCSCH₃ (OO/‖‖) OCH₂CH₃  Na⁺ | 2 | 8G 1C 6Y | 8G 2H | 8G 2C | 6G | 6G 3C | 0 | 3G |
| C₆H₅—CH₂OPCOCH₃ (OO/‖‖) OH  Na⁺ | 2 | 8G 5I 6Y | 8G 2H | 8G 2H | 0 | 4G | 0 | 0 |
| Na⁺  HOPCOCH₃ (OO/‖‖) OCH₂CH=CH₂ | 2 | 9C 10D | 7G 3C | 8C | 2G | 3G | 0 | 4G |
| Na⁺  HOPCSCH₃ (OO/‖‖) OCH₂CH=CH₂ | 2 | 9C 10D | 5G | 7G 2C | 0 | 2G | 0 | 2G |
| C₄H₉OPCOCH₂CH₃ (OO/‖‖) O⁻Na⁺ | 2 | 2C 5D | 8G | 10 C | 2G | 0 | 0 | 2G |
| Na⁺  HOPCOC₆H₁₃ (OO/‖‖) OC₄H₉ | 2 | 3C | 4G 1C | 6G | 0 | 0 | 0 | 3G |
| Na⁺  HOPCOC₆H₁₃ (OO/‖‖) OCH₃ | 2 | 2C | 4G | 4G | 3G | 0 | 0 | 0 |
| H₃COPCOCH₂CH(CH₃)CH₃ (OO/‖‖) OH  Na⁺ | 2 | 5G 1C | 5G | 3G | 0 | 0 | 0 | 0 |
| CH₃CH₂OPCOCH₂—C₆H₅ (OO/‖‖) O  Na⁺ | 2 | 9D | 5G 1C | 5G | 0 | 0 | 0 | 0 |
| C₄H₉OPCSCH₃ (OO/‖‖) OH  Na⁺ | 2 | 8G 4C 6Y | 9G | 6C | 1H | 2G | 0 | 2G |

| COMPOUND | Kg/Ha | Barnyard Grass | Wild Oats | Wheat | Corn | Soybean | Rice | Sorghum |
|---|---|---|---|---|---|---|---|---|
| H₃COPCOCH₃ (OO/‖‖) OH  Na⁺ | 2 | 7G 2C | 0 | 0 | 7G 2U | 6G | 0 | 6G 1C |
| HOPCSCH₃ (OO/‖‖) OCH₂CH₃  Na⁺ | 2 | 7G 2C | 0 | 2G | 7G 2U | 5G 1C | 0 | 7G 2U |

-continued

| | | POST EMERGENCE | | | | | | |
|---|---|---|---|---|---|---|---|---|
| 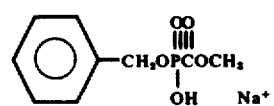 | 2 | 4G | 0 | 0 | 7G 2U | 6G | 0 | 1C |
|  | 2 | 7G 2C | 4G 2C | 4G | 7G 1C | 3G | 0 | 6G 1C |
| 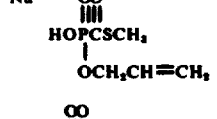 | 2 | 8G | 3G | 3G | 5G 1C | 5G | 0 | 5G 1C |
|  | 2 | 0 | 0 | 0 | 6G 2C | 0 | 0 | 0 |
|  | 2 | 0 | 0 | 0 | 6G 1C | 0 | 0 | 0 |
| 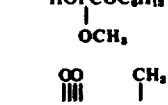 | 2 | 0 | 0 | 0 | 2G | 0 | 0 | 0 |
| 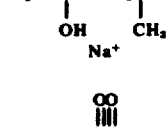 | 2 | 0 | 0 | 0 | 5G 1C | 0 | 0 | 0 |
| 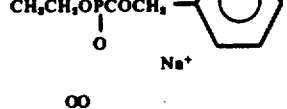 | 2 | 2C | 0 | 0 | 5G 1C | 0 | 0 | 0 |
| 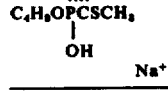 | 2 | 8C | 1H | 2G | 8G 1C | 9P | 2G | 7G 2C |

In another test, the test compounds were applied in a similar solvent to pots of bean (*Phaseolus vulgaris* cv. Black Valentine), apple (*Malus* sp.), and willow (*Salix* sp.). The plants were maintained in a greenhouse, and plant response ratings were taken after application as indicated.

| | | Black Valentine Bean | | Apple | | Willow | |
|---|---|---|---|---|---|---|---|
| | Rate, kg/ha | One Week | Four Weeks | One Week | Four Weeks | One Week | Four Weeks |
|  | 1 | 9G2H | 8G | 0 | 0 | 3G | — |
| | 4 | 10G | 8G | 0 | 0 | 9G5X | 5G3X |
| 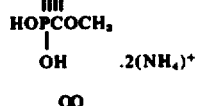 | 1 | 8G | 7G | 6G | 2G | 2G | 0 |
| | 4 | 10G10P 2C | 8G | 0 | 0 | 8G5X | 2G2X |
| 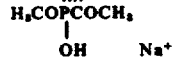 | 1 | 5G10P | 7G | 0 | 9G1C | 6G | 3G5X |
| | 4 | 9G10P | 9G5C | 0 | 10G | 10G | 9G5X |

-continued

| | Rate, kg/ha | Black Valentine Bean | | Apple | | Willow | |
|---|---|---|---|---|---|---|---|
| | | One Week | Four Weeks | One Week | Four Weeks | One Week | Four Weeks |
| $\text{HOPCSCH}_3$ with O=P(=O), OCH$_2$CH$_3$, Na$^+$ | 1 | 2G | 4G | 0 | 4G | 0 | 0 |
| | 4 | 8G10P | 9G | 0 | 6G | 9G | 9G3X |
| $\text{HOPCSCH}_3$ with O=P(=O), OCH$_2$CH$_3$, Na$^+$ | 1 | 9G10P | 10D | 0 | 6G | 6G | 8G5X |
| | 4 | 8G10P | 10G | 0 | 10G2C | 10G | 9G |
| $\text{CH}_3\text{CH}_2\text{OPCOCH}_3$ with O=P(=O), OH, Na$^+$ | 1 | 6G | 8G3X | 0 | 0 | 5G | 6G5X |
| | 4 | 8G10P | 10D | 1H | 10G2H | 9G | 9G3X |

The plant response ratings above are composed of a number and a letter. The number describes the extent of the response and ranges from zero to 10, with zero representing no response and 10 representing 100% response. As for the letters, G represents growth retardation, P represents terminal bud kill, H represents hormonal effects, C represents chlorosis, U represents unusual pigmentation, I represents increased chlorophyll, D represents defoliation, X represents axillary stimulation, 6Y* represents abscised buds or flowers, 7Y* represents a decreased number of buds or flowers, and 6F* represents delayed flowering.

*With the "6Y", "7Y", and "6F" ratings, the number does not refer to extent of response (any percent of bud or flower abscission is represented by "6Y").

The term "plant growth retardant" as used in this disclosure is to be understood to mean an agent which, when applied to a plant or its environs, will slow the growth of the plant. This also includes a delaying response on bud sprouting or prolonging of the dormancy period.

The compounds and salts of this invention can be applied as foliar sprays or as soil applications to retard the growth rate of such plants or to affect flowering and fruit set.

Preferably, the compounds and salts of this invention are applied as foliar or dormant wood sprays to the point of runoff, although lower-volume application can also be effective.

The compounds and salts of the invention are very versatile and may be applied at one of many different time periods to suit the convenience of the applicator. For example, they may be applied in spring a short time prior to the period when maximum plant growth is anticipated, to effect growth retardation; they may be applied later in the growing season, just after trimming, to effect growth retardation; or they may be applied when the year's growth has ceased (later summer, fall, or winter) with the result that treated plants will remain dormant the following spring; whereas untreated plants will sprout and grow. If flowering and fruit set are to be modified, the treatment is applied before, during, or shortly after flowering.

It will be recognized that the application rate is dependent upon the species to be treated and the results desired. In general, rates of from 0.25 to 20 kilograms per hectare are used, although higher or lower rates can achieve the desired effect in some instances.

Useful formulations of the compounds and salts of this invention can be prepared in conventional ways. They include dusts, granules, pellets, solutions, suspensions, emulsions, wetting powders, emulsifiable concentrates, and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Percent by weight | | |
|---|---|---|---|
| | Active Ingredient | Diluent(s) | Surfactant(s) |
| Wettable Powders | 20–90 | 0–74 | 1–10 |
| Oil Suspensions and Emulsions | 5–50 | 40–95 | 0–15 |
| Aqueous Solutions | 10–50 | 50–90 | 0–20 |
| Dusts | 1–25 | 70–99 | 0–5 |
| Granules and Pellets | 1–95 | 5–99 | 0–15 |
| High-strength Compositions | 90–99 | 0–10 | 0–2 |

Lower or higher levels of active ingredient can, of course, be present, depending on the intended use and the physical properties of the compound. Higher ratios of surfactant to active ingredient are sometimes desirable and are achieved by incorporation into the formulation or by tank-mixing. Likewise, high levels of oils or humectants can be incorporated, either in the formulation or by tank-mixing.

Typical solid diluents are described in Watkins et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., N.Y., 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine, solid compositions are made by blending and, usually, grinding, as in a hammer or fluid energy mill. Suspensions are prepared by wet-milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147 ff. and "Perry's Chemical Engineer's Handbook", 4th Ed., McGraw-Hill, N.Y., 1963, pp. 8–59 ff.

For further information regarding the art of formulation, see, for example:
- H. M. Loux, U.S. Pat. No. 3,235,361, Feb. 15, 1966, Col. 6, line 16 through Col. 7, line 19, and Examples 10 through 41
- W. P. Langsdorf, U.S. Pat. No. 3,627,507, Dec. 14, 1971, Col. 8, line 1, through Col. 11, line 12, and Examples 60–65
- G. C. Klingman, "Weed Control as a Science", John Wiley & Sons, Inc., N.Y., 1961, pp. 81–96
- J. D. Fryer and S. A. Evans, "Weed Control Handbook", 5th Ed., Blackwell Scientific Publications, Oxford, 1968, pp. 101–103

The following Examples further illustrate the formulation and application of the compounds of this invention.

EXAMPLE 13

Water-soluble Powder

| | |
|---|---|
| diammonium methoxycarbonylphosphonate | 95.0% |
| dioctyl sodium sulfosuccinate | 0.5% |
| sodium ligninsulfonate | 1.0% |
| synthetic fine silica | 3.5% |

The ingredients are blended and coarsely ground in a hammer mill so that only a small percent of the active exceeds 250 microns (U.S.S. No. 60 sieve) in size. When added to water with stirring, the coarse powder initially disperses and then the active ingredient dissolves so that no further stirring is needed during application.

Ten kilograms of this formulation are dissolved in 800 liters of water containing 0.5% of a nonphytotoxic wetting agent. This formulation is sprayed from a helicopter to a one-hectare area under an electric power line in which the brush and trees have been freshly trimmed. This treatment retards the growth of black willow (*Salix nigra*), black cherry (*Prunus serotina*), and many other woody species.

The following can be formulated and applied in a similar manner with similar results.
ethyl sodium methoxycarbonylphosphonate
methyl sodium methoxycarbonylphosphonate
methyl sodium ethoxycarbonylphosphonate
ethyl sodium ethoxycarbonylphosphonate
ethyl sodium (methylthio)carbonylphosphonate
methyl sodium (ethylthio)carbonylphosphonate

EXAMPLE 14

Wettable Powder

| | |
|---|---|
| diammonium methoxycarbonylphosphonate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All solid compounds of the invention may be formulated in the same manner.

Fifteen kilograms of this formulation are mixed with 600 liters of water in a sprayer fitted with an agitator. The mixture is sprayed on a 1 hectare area of newly trimmed hedgerow in the spring after the leaves have expanded. (The spray may be either directly on the plants or to the locus of the plants.) This treatment greatly reduces the growth of plants growing in the hedgerow but does not seriously injure them. Thus, the hedgerow is kept neat with a minimum of labor expended for trimming it.

EXAMPLE 15

Solution

| | |
|---|---|
| methoxycarbonylphosphonic acid | 20.0% |
| octylphenoxypolyethoxyethanol | 0.5% |
| water | 79.5% |

The ingredients are combined and stirred to produce a solution which can be applied directly or after dilution with additional water. All sufficiently soluble compounds of the invention may be formulated in similar fashion.

Fifteen liters of this solution are mixed with 200 liters of water and sprayed in late Summer on a 1 hectare area of woody plants growing on a power line right-of-way. The treated plants continue to appear like untreated plants. However, the following year the treated plants remain dormant for an extremely long period of time, whereas untreated ones sprout and grow normally. Thus the treatment greatly reduces the amount of labor required to maintain the plants at a desirable height.

I claim:

1. A method of retarding plant growth consisting essentially of applying to the plant an effective amount of

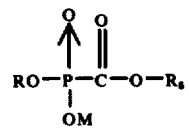

wherein
R is M; alkyl of 1 to 8 carbon atoms, optionally substituted with a chlorine, bromine, fluorine, or iodine; alkenyl of 3 to 8 carbon atoms; or

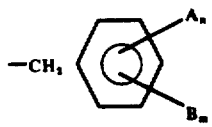

wherein
A is chlorine or methyl,
B is chlorine or methyl,
n is 0 or 1, and
m is 0 or 1;
$R_5$ is alkyl of 1 to 6 carbon atoms, alkenyl of 3 to 4 carbon atoms, or benzyl;
M is hydrogen, sodium, lithium, potassium, calcium, magnesium, zinc, manganese, barium, or

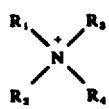

wherein
$R_1$ is hydrogen, alkyl of 1 to 4 carbon atoms, or hydroxyalkyl of 2 to 4 carbon atoms;
$R_2$ is hydrogen, alkyl of 1 to 4 carbon atoms, or hydroxyalkyl of 2 to 4 carbon atoms;
$R_3$ is hydrogen, alkyl of 1 to 4 carbon atoms, or hydroxyalkyl of 2 to 4 carbon atoms; and
$R_4$ is hydrogen or alkyl of 1 to 12 carbon atoms, provided that the total number of carbon atoms in $R_1$, $R_2$, $R_3$, and $R_4$ is less than 16.

2. The method of claim 1 wherein
R is hydrogen, alkyl of 1 to 4 carbon atoms, or benzyl;
$R_5$ is alkyl of 1 to 4 carbon atoms; and
M is hydrogen, sodium, potassium, or ammonium.

3. The method of claim 2 wherein the compound is ethyl sodium methoxycarbonylphosphonate.

4. The method of claim 2 wherein the compound is methyl sodium methoxycarbonylphosphonate.

5. The method of claim 1 wherein the compound is diammonium methoxycarbonylphosphonate.

6. The method of claim 2 wherein the compound is methoxycarbonylphosphonic acid.

7. The method of claim 2 wherein the plant is a woody plant.

8. The method of claim 2 wherein the plant is a viney plant.

9. The method of claim 2 wherein the plant is a grass.

* * * * *